(12) United States Patent
Jennings et al.

(10) Patent No.: US 9,757,501 B2
(45) Date of Patent: Sep. 12, 2017

(54) METHODS AND APPARATUS FOR LOWERING INTRACRANIAL AND INTRASPINAL CORD PRESSURE

(71) Applicants: Thomas Jennings, Dallas, TX (US); David B Gillis, League City, TX (US)

(72) Inventors: Thomas Jennings, Dallas, TX (US); David B Gillis, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 857 days.

(21) Appl. No.: 13/858,703

(22) Filed: Apr. 8, 2013

(65) Prior Publication Data

US 2013/0274638 A1   Oct. 17, 2013

Related U.S. Application Data

(60) Provisional application No. 61/623,710, filed on Apr. 13, 2012.

(51) Int. Cl.
| | |
|---|---|
| *A61H 7/00* | (2006.01) |
| *A61M 1/00* | (2006.01) |
| *A61H 9/00* | (2006.01) |
| *A61M 16/04* | (2006.01) |

(52) U.S. Cl.
CPC ......... *A61M 1/0066* (2013.01); *A61H 9/0057* (2013.01); *A61M 1/0031* (2013.01); *A61M 1/0088* (2013.01); *A61H 7/008* (2013.01); *A61M 1/0037* (2013.01); *A61M 16/0465* (2013.01); *A61M 2210/06* (2013.01); *A61M 2210/086* (2013.01); *A61M 2210/1021* (2013.01)

(58) Field of Classification Search
CPC .............. A61M 1/0066; A61M 1/0031; A61M 1/0037; A61M 2210/06; A61M 2210/1021; A61H 9/0057; A61H 7/008
See application file for complete search history.

(56) References Cited

U.S. PATENT DOCUMENTS

| | | | | |
|---|---|---|---|---|
| 5,938,626 A | * | 8/1999 | Sugerman | A61B 17/42 600/561 |
| 7,195,012 B2 | | 3/2007 | Lurie | |
| 2003/0167018 A1 | * | 9/2003 | Wyckoff | A61F 5/56 600/538 |
| 2006/0266369 A1 | * | 11/2006 | Atkinson | A61F 5/566 128/848 |

(Continued)

OTHER PUBLICATIONS

Eckberg D., et al. Respiratory and Baroreceptor Reflex Interactions in Man. May 1977 Journal of Clinical Investigation, 59, 780-785.*

(Continued)

*Primary Examiner* — Justine Yu
*Assistant Examiner* — Timothy Stanis
(74) *Attorney, Agent, or Firm* — Blank Rome, LLP

(57) ABSTRACT

Apparatus and methods are provided for applying negative pressure to tissues of a patient that are transmitted to the vertebral venous system of the patient and thereby lowering intracranial pressure. Intracranial pressure is thus lowered easily without increasing the work of breathing, without needing to be intubated, and without breathing through a valve in patients with elevated increased intracranial pressure.

14 Claims, 5 Drawing Sheets

(56) References Cited

U.S. PATENT DOCUMENTS

| | | | | |
|---|---|---|---|---|
| 2008/0115786 A1* | 5/2008 | Sinderby | .............. | A61H 31/02 128/204.23 |
| 2009/0062701 A1* | 3/2009 | Yannopoulos | ....... | A61H 9/0078 601/41 |
| 2009/0234263 A1* | 9/2009 | Doel | .................. | A61F 5/05816 602/13 |
| 2010/0137951 A1* | 6/2010 | Lennox | .................... | A61F 7/02 607/104 |
| 2010/0319691 A1* | 12/2010 | Lurie | .................... | A61H 31/02 128/203.12 |
| 2011/0066094 A1* | 3/2011 | Thorgilsdottir | ........ | A61F 5/055 602/6 |
| 2011/0190845 A1* | 8/2011 | Weisfeldt | .......... | A61B 5/04001 607/42 |
| 2014/0343599 A1* | 11/2014 | Smith | ............... | A61B 17/1325 606/202 |

OTHER PUBLICATIONS

Eckberg D., Influence of Weightlessness Upon Human Autonomic Cardiovascular Control. 1978. Life Sciences Data Archive, Johnson Space Center. https://lsda.jsc.nasa.gov/scripts/experiment/exper.aspx?exp_index=3 and https://lsda.jsc.nasa.gov/lsda_data/dil_data/55233019.jpg.*

Cooper, Victoria L. et al., Cartoid Baroreflex Testing Using the Neck Collar Device, Clin Auton Res (2009) 19: 102-112.*

Rangel-Castillo, Leonardo et al., Management of Intracranial Hypertension, Neurol Clin (2008) 26(2): 521-541.*

Bath E, Lindblad LE, Wallin BG, Effects of Dynamic and Static Neck Suction on Muscle Nerve Sympathetic Activity, Heart Rate and Blood Pressure in Man. J. Physiol. (1981) vol. 311, pp. 551-564.

Chibis Lower-Body Negative-pressure suit. Product catalogue page. http://www.zvezda-npp.ru/engl/chibis.html. 2007.

Convertino VA, et. al. Optimizing the Respiratory Pump: Harnessing Inspiratory Resistance to Treat Systemic Hypotension. Respiratory Care (2011) vol. 56(6), pp. 846-857.

Gazenko OG, et. al. Effects of Various Co.untermeasures Against the Adverse Effects of Weightlessness on Central Circulation in the Healthy Man. Aviation, Space, and Environmental Medicine. (1982) vol. 53 (6), pp. 523-530.

Goswami N., et. al. "LBNP: Past Protocols and Technical Considerations for Experimental Design" Aviation, Space and Environmental Medicine (2008) vol. 79, pp. 459-471.

Keyl C, et. al. Sinusoidal Neck Suction for Evaluation of Baroreflex Sensitivity During Desflurane and Sevoflurane Anesthesia. (2002) vol. 95, pp. 1629-1636.

EDL E-2000 Neck Baro Reflex System. Blood Pressure Control. NASA Spinoff Data Base Record 1992, p. 81.

Ogoh S, et. al., Does pulsatile and sustained neck pressure or neck suction produce differential cardiovascular and sympathetic responses in humans? Experimental Physiology. (2003) vol. 88.5, pp. 595-601.

Philadelphia Tracheotomy Collar. Order Information. http://www.ossur.com/?PageID=13504. Dec. 13, 2011.

Potts JT and Raven PB. "Effect of dynamic exercise on human carotid-cardiac baroreflex latency" Am. J. Physiol. (1995) vol. 268 (Heart Circ. Physiol. 37) pp. H1208.-H1214.

Saggi BH, et al. "Treatment of intracranial hypertension using nonsurgical abdominal decompression" J Trauma. (1999) vol. 46, pp. 646-651.

Sprenkle JM, et. al., Device for rapid quantification of human carotid baroreceptor-cardiac reflex responses. J. Appl. Physiol. (1986) vol. 60(2), pp. 727-732.

Yannopoulos D. et al. "Intrathoracic pressure regulation for intracranial pressure management in normovolemic and hypovolemic pigs" Crit. Care. Med. (2006) vol. 34[Suppl.], pp. S495-S500.

Yingthawornsuk T, et. al. Identification of Open-Loop Transfer Functions in Closed-Loop Baroreflex System using Random Breathing in Humans. Computers in Cardiology (2002) vol. 29, pp. 461-464.

* cited by examiner

METHODS AND APPARATUS FOR LOWERING INTRACRANIAL AND INTRASPINAL CORD PRESSURE

CROSS REFERENCE TO RELATED APPLICATIONS

This application claims priority based on U.S. Provisional Application Ser. No. 61/623,710 filed Apr. 13, 2012, which is incorporated herein by reference.

FIELD OF THE INVENTION

This invention relates generally to apparatus and methods for reducing harmful pressure within the cranium and spinal cord.

BACKGROUND OF THE INVENTION

Without limiting the scope of the invention, its background is described in connection with problems associated with increased intracranial and spinal cord pressure and existing modalities for relieving such pressure.

Elevated intracranial pressure (ICP) is a significant medical problem for several reasons. Elevated ICP and CNS edema are critical element of traumatic brain and spinal cord injury. Traumatic Brain Injury (TBI) accounts for approximately 40% of all deaths from acute injuries in the United States. Persistent elevated ICP and disc edema has been found in some astronauts after prolong space flight. The extent of this problem is unknown, but its solution is considered to be mission-critical. Intracranial pressure can damage the brain or spinal cord by compressing brain tissue and restricting blood flow, which results in decreased cerebral perfusion pressure ("CPP"). Failure to quickly remedy excessive ICP may result in transient and permanent neurological problems, seizures, stroke, herniation of the brain and death.

Abnormal increases in intracranial pressure ("ICP") can result from increased cerebral spinal fluid ("CSF") pressure or directly from increased pressure within the closed cranial vault such as that resulting from growth of intracranial mass, intracranial bleeding, fluid accumulation around the brain, or swelling of brain tissues. Whether resulting from an infectious process, pathophysiologic condition, or trauma, significantly raised intracranial pressure is a medical emergency.

Existing acute treatments for increased ICP include draining of cerebrospinal fluid, administration of medications to decrease swelling, and, if necessary, removal of part of the skull. Clearly, each of these treatments is particularly difficult and not completely efficacious.

From the foregoing it is apparent the there is a need in the art for methods and apparatus that are able to non-invasively reduce ICP. The invention described herein provides novel methods and apparatus for reducing ICP by providing negative inspiratory pressure without intubation.

BRIEF SUMMARY OF THE INVENTION

The present invention is directed to methods and apparatus for reducing intracranial pressure. In one embodiment, an intracranial pressure modulation apparatus is provided that includes a shell shaped and dimensioned to fit a ventral aspect of a neck of a patient and that is held in place with a strap. The shell includes a gasket attached to an inner surface of the shell and adapted and dimensioned to form at least one negative pressure chamber between the shell and the neck of the patient. The shell and gasket are dimensioned to avoid placing positive pressure against the carotid sinus of the patient. In certain embodiments the neck shell and gasket includes an opening over the trachea of the patient. The negative pressure chamber is evacuated through a suction port in communication with the negative pressure chamber. The chamber may be evacuated with hand pump, particularly for emergency applications, or via a mechanical pump. Application of negative pressure can be constant, delivered according to a cycling schedule or inputted program or applied in synchrony with a respiration cycle of the patient.

In other embodiments, a system for decreasing intracranial pressure in a patient in need thereof is provided that includes a negative pressure chamber that is dimensioned and adapted to fit against a tissue of the patient, a programmable pump attached to the negative pressure chamber and dimensioned to apply between 5 and 60 mmhg negative pressure to the tissue and an inspiration detector attached to the pump, wherein the pump pulls negative pressure on the tissue that is coincident with detected inspiration. In certain embodiments the tissue is a neck tissue. In other embodiments, the tissue is an abdominal tissue. In such embodiments the system may further include at least one occlusive band adapted and dimensioned to fit around a leg of the patient and retard venous return as desired.

BRIEF DESCRIPTION OF THE DRAWINGS

For a more complete understanding of the present invention, including features and advantages, reference is now made to the detailed description of the invention along with the accompanying figures.

DETAILED DESCRIPTION OF THE INVENTION

While the making and using of various embodiments of the present invention are discussed in detail below, it should be appreciated that the present invention provides many applicable inventive concepts that can be employed in a wide variety of specific contexts. The specific embodiment discussed herein are merely illustrative of specific ways to make and use the invention and do not limit the scope of the invention.

Previous work has found that applying negative inspiratory pressure instantaneously lowers intracranial pressure and that this reduction persists over time with continued enhanced negative inspiration pressure. See e.g. D Yannopoulos et al. "Intrathoracic pressure regulation for intracranial pressure management in normovolemic and hypovolemic pigs" *Crit. Care. Med.* 34 [Suppl.] (2006) S495-S500. Other authors have found that intrathoracic pressure changes are transmitted to the intracranial pressure via the vertebral venous system and not by either the carotid artery or internal jugular veins. However, one problem with increasing the negative pressure of inspiration is that the patient needs to be either intubated or breathe through a valve to create the additional negative inspiratory pressure. Breathing through this valve doubles the work of breathing.

Disclosed herein are novel methods and apparatus for applying negative inspiratory pressure to lower intracranial pressure ("ICP") via the vertebral venous system, which is in connection with the cerebral spinal fluid ("CSF") along the entire length of the central nervous system. Importantly, if there is an obstructive lesion, the pressure drop will not precipitate herniation since the pressure would be reduced above and below the lesion simultaneously.

While the methods and apparatus disclosed herein may be most commonly utilized for treatment of disease and injury resulting in increased ICP, they are also suitable in other abnormal ICP states including for example, zero gravity. Thus, the methods and apparatus may be utilized by astronauts to prevent cephalad fluid accumulation and increased intracranial pressure.

Figure 1:
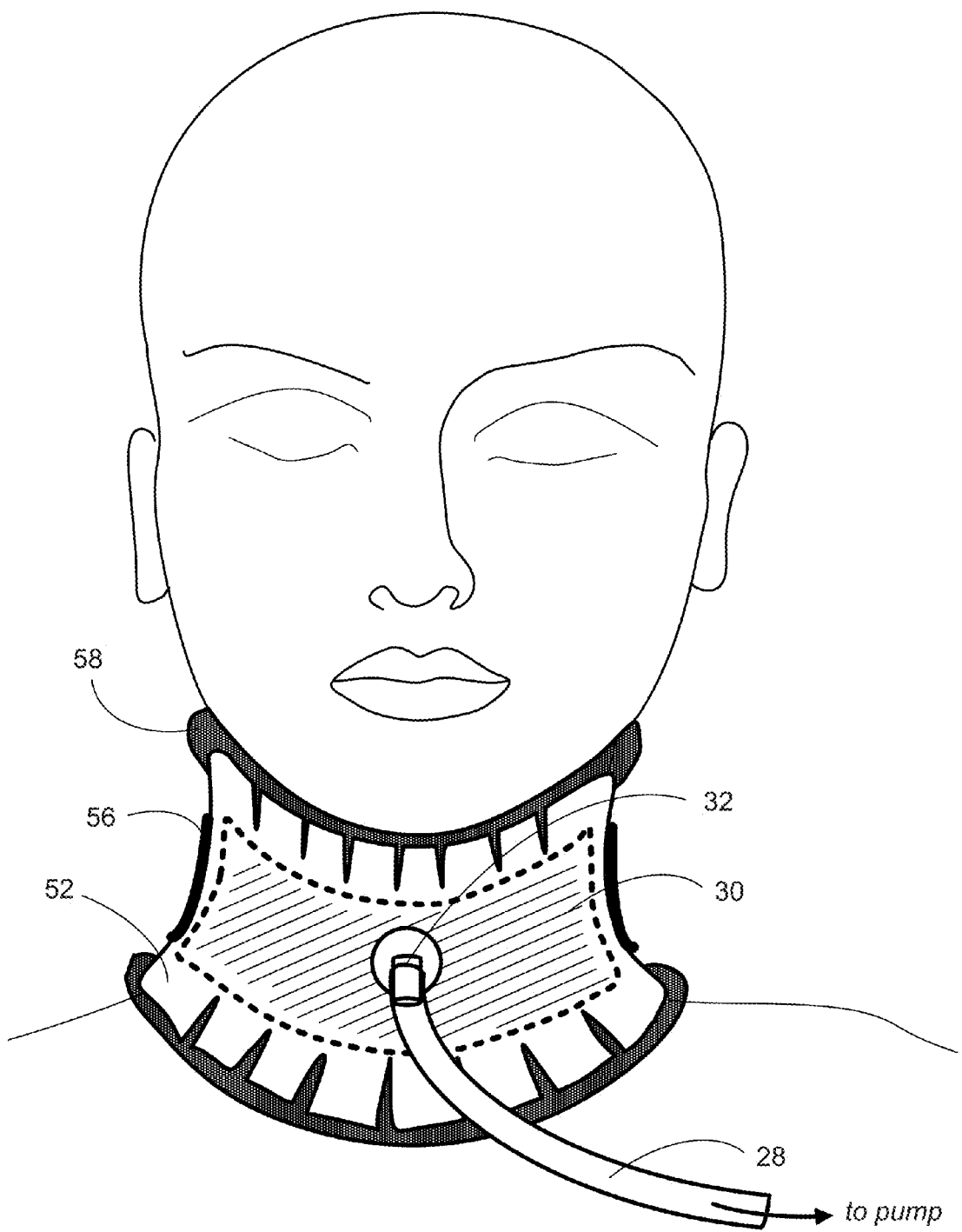
FIG. 1 graphically depicts a front view of an embodiment of an ICP modulation collar.

In one embodiment disclosed herein negative pressure is generated around portions of the neck. In other embodiments, the negative pressure is applied to the chest and/or lower abdomen. The application of negative pressure may be applied constantly, cycled based on the patient's inspiration, set to cycle at a preset rate, or synced with ICP. This method would be comparatively unobtrusive for the patient (FIG. 1). Negative pressure generated through cervical tissues is transmitted to the vertebral venous system and thereby lowers intracranial pressure. Intracranial pressure is thus lowered easily without increasing the work of breathing, without needing to be intubated, and/or without breathing through a valve in patients with elevated increased intracranial pressure.

In certain embodiments a system is provided in which negative pressure devices are provided together with monitoring of the ICP and/or jugular venous flow and the application of negative pressure is implemented by a pump controllable to cycle between negative pressure and zero pressure according to an inputted program. In other embodiments the pump is controlled on the basis of desired levels of ICP and/or jugular vein flow rate and/or pressure.

ICP may be determined by several methods known to those of skill in the art. Invasive devices include intraventricular catheters, fiberoptic monitors, subarachnoid bolts and epidural pressure transducers. ICP may also be monitored non-invasively by transcranial Doppler ultrasound (TCD), Single Photon Emission Computerized Tomography (SPECT), and Continuous Electroencephalogram (EEG) Monitoring.

Negative pressure may be applied continuously, according to a preset protocol or synchronized with patient respiration. A normal adult human has a respiratory rate of 12-15 breaths/minute at rest, inspiring and expiring 6-8 liters/minute of air. Respiration can be detected by various methods known to those of skill in the art including without limitation sensing inspiratory and/or expiratory air flow by any one of temperature, humidity, $O_2$ and/or $CO_2$, or acoustic sensing. Respiration can also be measured by detecting thoracic or abdominal circumference movement using strain gauges, etc.

In certain embodiments, further parameters are considered in the application of negative pressure including the amount of negative pressure that is applied, the rate of application, the release of negative pressure, the rate of pressure release, the relationship to the patient's respiratory cycle. A computer device that monitors ICP values is utilized to adjust and optimize negative pressure application by adjusting one or more of the above further parameters while determine the effect of the adjustment on ICP and then making further iterative adjustments.

In certain embodiments, the negative pressure is applied at a level of about −5 mmHg to about −100 mm Hg. In other embodiments the negative pressure range is from about −20 mmHg to −60 mmHg. As used herein, 1 mmHg is considered approximately equal to 1 Torr.

The negative pressure provided may be constant, cyclical but independent of respiratory rate or dependent on respiratory rate. In certain embodiments where the negative pressure is cyclical but independent of the respiratory cycle, cycling rates in a range of from 1 cycle/min to 60 cycles/min are provided. In certain embodiments, application of minimum pressure and release to atmospheric ramped to the extent permitted by the cycling rate in order for the procedure to be better tolerated by the patient.

The following examples are included for the sake of completeness of disclosure and to illustrate the methods of making the compositions and composites of the present invention as well as to present certain characteristics of the compositions. In no way are these examples intended to limit the scope or teaching of this disclosure.

Example 1: Negative Pressure Applied to Decrease ICP

Figure 4:
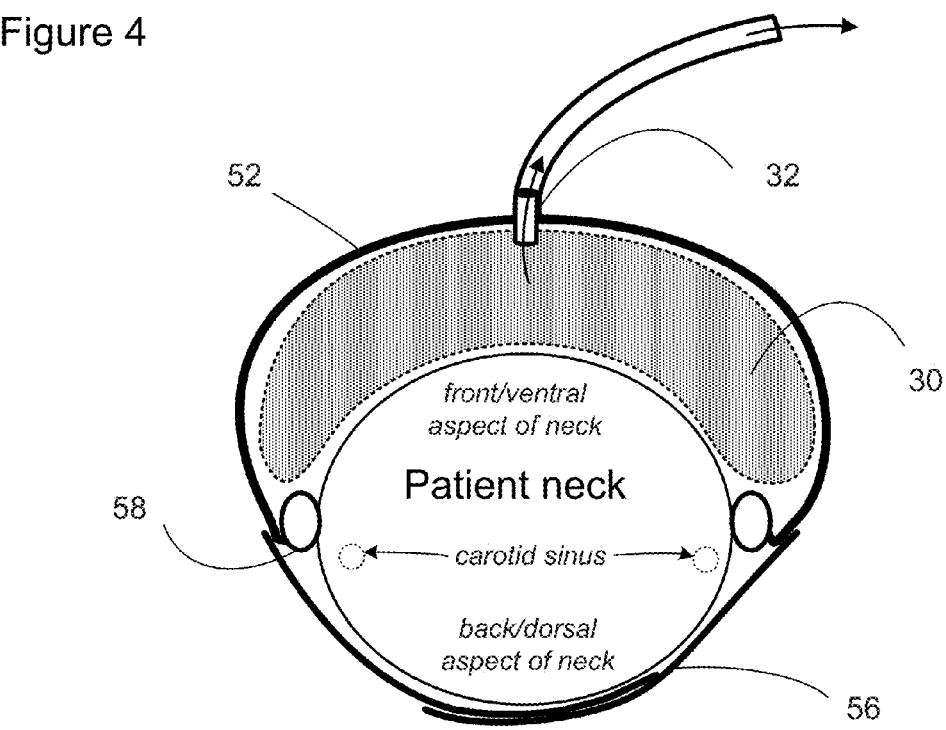
FIG. 4 depicts a top down view of one embodiment of an ICP modulation collar having a single negative pressure chamber.

In one embodiment as depicted in FIG. 1, a negative pressure ICP modulation device is provided wherein a soft flexible seal material or gasket 58 attached along the edge of a shell 52 that forms a seal against the front and a portion of the sides of the patient's neck. The shell is sufficiently rigid to resist collapse upon application of negative pressure and the shell and seal together create a pressure controllable space between the neck and the shell. The negative pressure device is held in place with a fastener strap 56 that wraps around the back of the patient's neck. Suction port 32 is attached to the shell for attachment with a suction hose 28. This hose is connected to a pump. The pump sucks air out of the space 30 between the shell and neck and creates the negative pressure around the neck. The application of negative pressure may be applied constantly, cycled based on the patient's inspiration, set to cycle at a preset rate, or synced with ICP monitoring. FIG. 4 depicts a top down view of an embodiment generally in accordance with FIG. 1.

Figure 2:
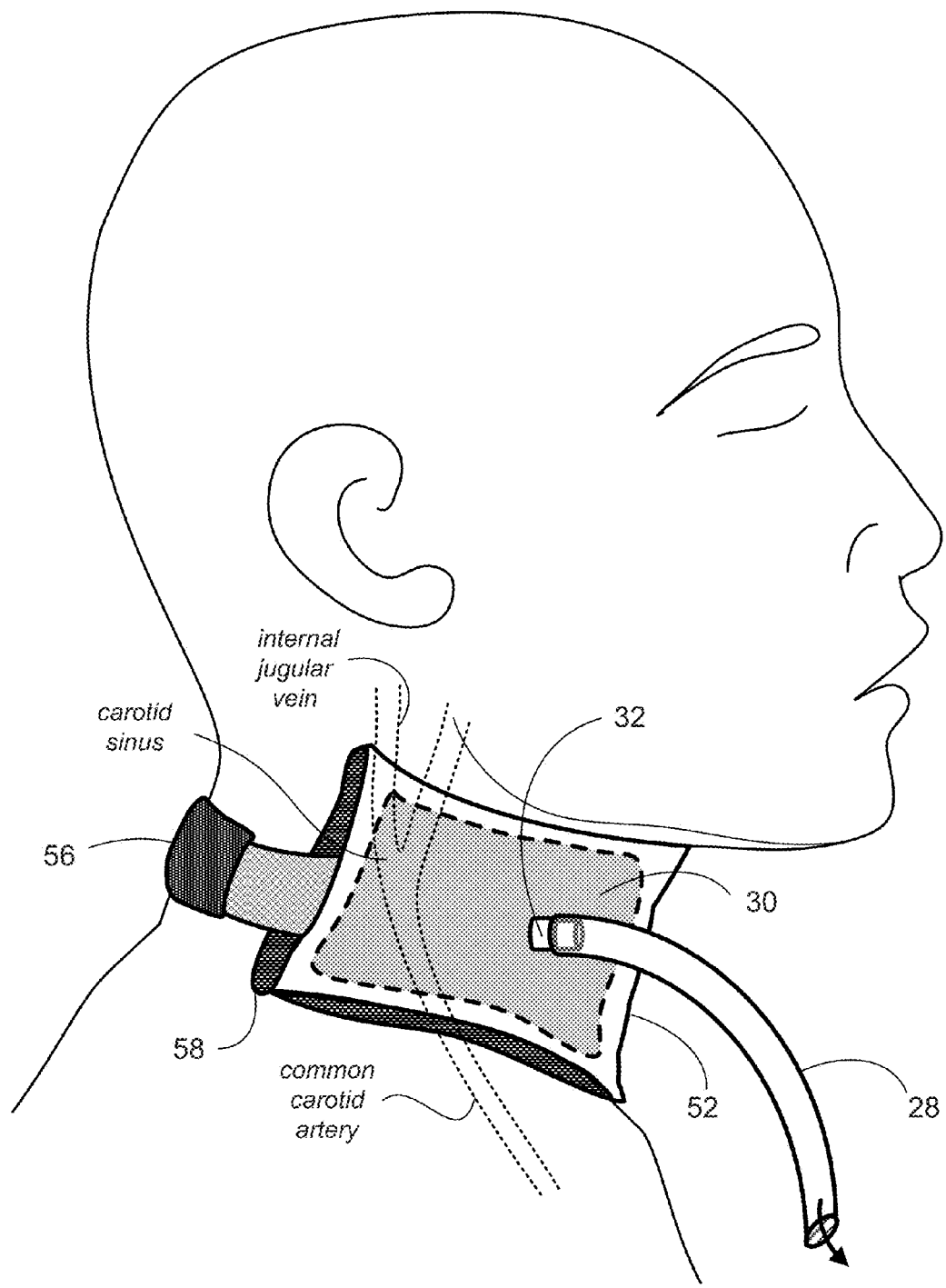
FIG. 2 graphically depicts a side view of an embodiment of an ICP modulation collar showing the underlying position of the carotid sinus.

FIG. 2 presents aspects of an embodiment generally depicted in accordance with FIG. 1. The depicted embodiment differs from neck positive pressure devices such as the E-2000 Neck Baro Reflex System, Engineering Development Laboratories, Newport News, Va. in several important ways. Carotid baroreflex (CBR) function has been extensively studied in humans by the application of neck pressure (NP) and neck suction (NS) to the carotid sinus using variable pressure neck chambers such as the E-2000 Neck Baro Reflex System. These studies have shown that positive and negative pressure applied over the carotid sinuses, whether steady or pulsatile, results in changes in heart rate. See e.g. S Ogoh, et al. "Does pulsatile and sustained neck pressure or neck suction produce differential cardiovascular and sympathetic responses in humans?" *Experimental Physiology* 88.5 (2003) 595-601; J T Potts and P B Raven "Effect of dynamic exercise on human carotid-cardiac baroreflex latency" *Am. J. Physiol.* 268 (Heart Circ. Physiol. 37): (1995) H1208.-H1214.

As shown in FIG. 2, the device is dimensioned to avoid pressure on receptors situated in the carotid sinus. The carotid sinus is a dilatation of the lower end of the internal carotid artery. The carotid sinus receptors are baroreceptors (a stretch receptor) located in the carotid sinuses of the left and right internal carotid arteries. These baroreceptors monitor the pressure of the blood being delivered to the brain. At normal resting blood pressures, baroreceptors discharge with each heartbeat. When blood pressure falls, baroreceptor firing rate decreases and baroreceptor reflexes help restore blood pressure by increasing heart rate. Impulses from the sinus travel up the carotid sinus nerve to the nucleus of the tractus solitarius (NTS) in the medulla. Stimulation of the vagal nuclei in the medulla results in reduced heart rate (bradycardia). NTS stimulation further inhibits sympathetic nerve impulses to peripheral blood vessels, which results in vasodilatation and thus reduced blood pressure.

In the embodiment depicted in FIG. 2, the negative pressure chamber 30 will not apply positive pressure to the carotid sinuses, so the carotid sinuses are not stimulated by the device. The negative pressure generated would cycle between negative value and zero. In certain embodiments, negative pressure generation is coupled to patient inspiration.

Example 2: Negative Pressure System in a Tracheotomy Collar

Figure 3:
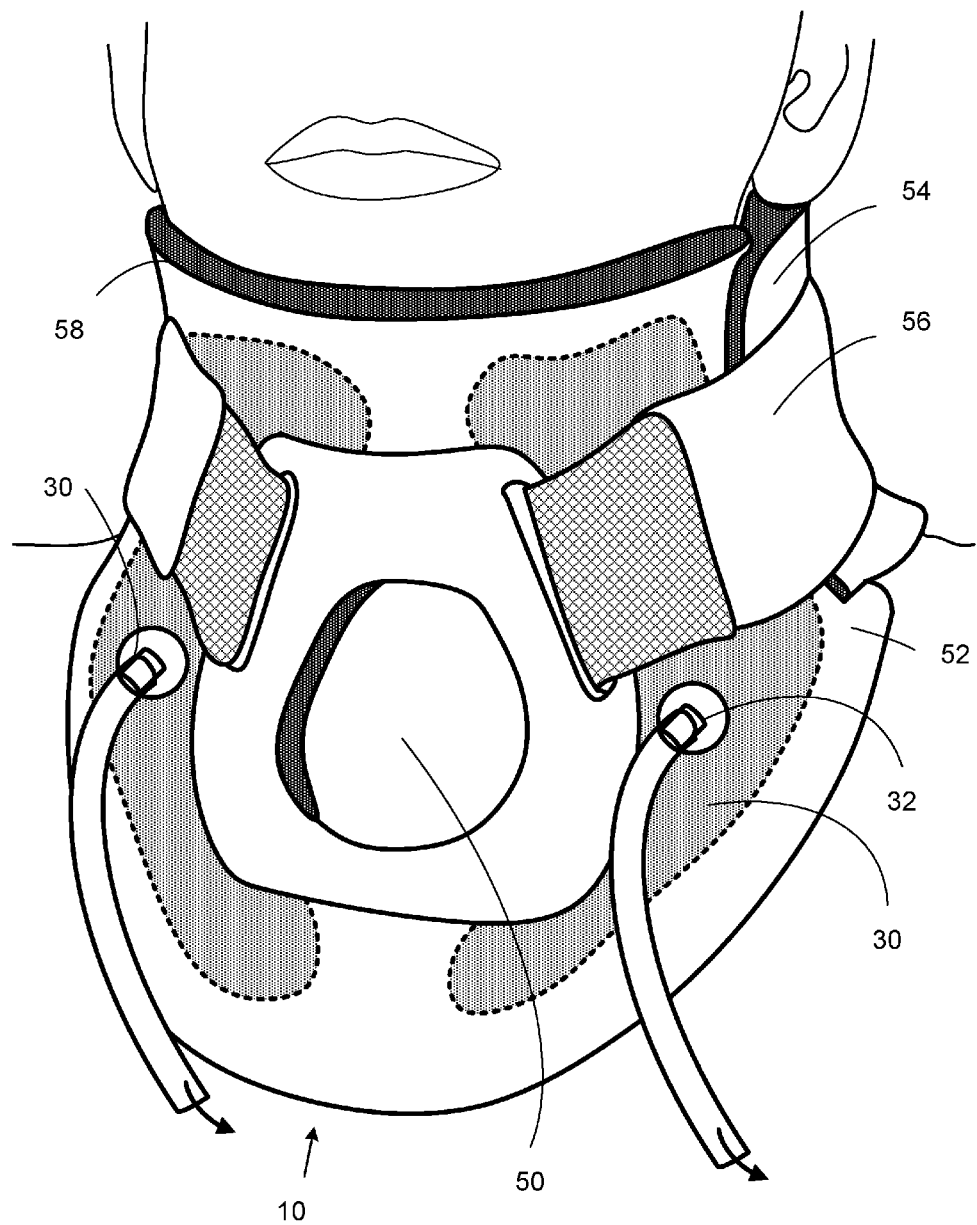
FIG. 3 graphically depicts an ICP collar including accessibility for a tracheotomy according to one embodiment.

In another embodiment, depicted in FIG. 3, the inventors' negative pressure concept is applied to situations where the patient has an existing tracheotomy or is reasonably anticipated to need a tracheotomy in the future, in particular with head/spinal cord trauma patients at the scene of an accident to prevent increased ICP, which would damage the brain or spinal cord.

Tracheotomy cervical collar 10 includes a central collar opening 50 for a tracheotomy such as for example a Philadelphia® brand tracheotomy collar. A Philadelphia® brand tracheotomy collar will typically feature a relatively large central collar opening 50 over the trachea for quick access to carotid pulse monitoring and emergency tracheotomy if needed. As depicted in FIG. 3, a tracheotomy collar according to one embodiment disclosed herein includes one or more negative pressure chambers 30. Negative pressure may be provided via a single chamber with a central hole sealed against the neck tissues and aligning with central opening 50 or may be provided by several chambers such as one chamber 30 on each side of the central ventral tracheostomy hole 50 as depicted. Each negative pressure chamber 30 is provided with a suction port 32. The number of suction ports 32 will be determined by the number of negative pressure chambers.

Figure 5:
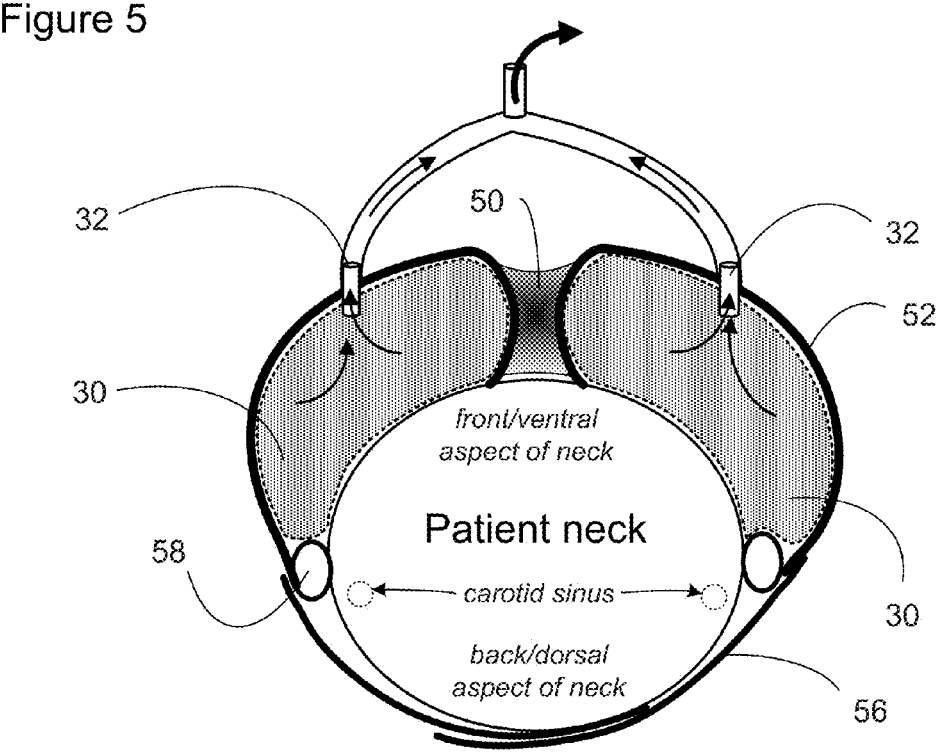
FIG. 5 depicts a top down view of one embodiment of an ICP modulation collar including accessibility for a tracheotomy.

The collar may be constructed as depicted with a front/ventral piece 52 and an over- or under-lapping back/dorsal piece 54 although other designs would be suitable as well. In the depicted embodiment, the front and back pieces are held together with strap 56, which is held in place with hook and loop fastening such as with Velcro® brand hook and loop fastening. Other types of fasteners including for example snaps, elastic cords and the like may be suitable as well. At least the front piece including negative pressure chamber(s) is a contoured, molded shell of sufficient rigidity to avoid collapse when negative pressure is created within the shell. The shell padding or gasket 58 provides a comfortable fit but also creates the margins of the negative chamber and is fitted sufficiently snuggly to the neck that negative pressure may be formed by evacuating air from the chambers through suction port(s) 32. Typically the entire construction will be water-resistant, non-toxic, hypoallergenic, and translucent to X-ray, CT and MRI modalities. FIG. 5 depicts a top down view of another tracheotomy cervical collar embodiment generally in accordance with FIG. 3.

Negative pressure is applied by evacuating a space 30 within the shell through a suction port such as suction port 32 attached to the shell for attachment with a suction hose 28. The space may be evacuated by a manual pump, as may be particular suitable for emergency devices, or using an electronically controlled mechanical pump that is set to apply negative pressure constantly, cycled based on the patient's inspiration, set to cycle at a preset rate, or synced with ICP monitoring.

Example 3: Negative Pressure System Implemented Regionally to Reduce ICP

In another embodiment, a negative pressure device is adapted and dimensioned for placement around a region of the body. In one embodiment the region is the lower abdomen. Cerebral venous outflow is via two systems: the vertebral venous plexus and the internal jugular veins. Vertebral venous plexus is more prominent in the upright position and internal jugular system is more prominent in the supine position.

The vertebral venous plexus is connected to the subarachnoid space along the entire length of the spinal cord and veins surrounding the brain. The vertebral venous plexus is thought to be involved in CSF reabsorption. Elevated intra-abdominal pressure (IAP) can cause elevated intracranial pressure (ICP) and reduced cerebral perfusion pressure (CPP) and is in particular a feature of life threatening Abdominal Compartment Syndrome (ACS). Solutions tested for lowering IAP in ACS have included decompressive laparotomy and application of Continuous Negative Abdominal Pressure (CNAP). See Saggi B H, et al. "Treatment of intracranial hypertension using nonsurgical abdominal decompression" J Trauma 46 (1999) 646-651). However, using abdominal negative pressure in patients or animals with a normal intra-abdominal pressure has no effect on ICP. Id. Saggi et al.

Negative pressure has been applied to the lower body and extremities to counteract the blood volume redistribution that occurs during space. Undesired blood volume redistribution has been controlled by leg occlusion cuffs attached around the upper third of the femur that allow for arterial supply to the legs but restrict return venous flow as well as by Local Negative Pressure ("LNP") "stockings" applied just above the knees and regional Lower Body Negative Pressure (LBNP) applied to both legs in a unitary device fitted across the level of the iliac crests. LBNP was adapted to an ambulatory "Chibis" suit worn by cosmonauts that enclosed the legs and groin and was secured by air airtight belt below the iliac crest of the pelvis. Using the Chibis suit, negative pressure applied to the legs caused blood pooling in legs to counteract orthostatic hypotension. See Goswami, N., et al. "LBNP: Past Protocols and Technical Considerations for Experimental Design" Aviation, Space and Environmental Medicine 79 (2008) 459-71; Gazenko et al. "Effects of Various Countermeasures Against the Adverse Effects of Weightlessness on Central Circulation in the Healthy Man" Aviation, Space and Environmental Medicine 53 (6) (1982) 523-530.

In contrast to the lower extremity negative pressure that has been applied to effect blood pooling and control orthostatic stress in weightlessness, in one embodiment disclosed herein, a pulsating negative pressure, from 0 mm Hg to a negative pressure of from −5 to −60 mmHg, is applied to a patient's abdomen and is synchronized with the patient's respiration (most likely with inspiration) to lower lumbar intrathecal pressure and by extension ICP. The negative pressure on the patient's abdomen creates a negative pressure in the abdominal veins that will extend through the inferior vena cava and azygos veins to the lumbar anterior spinal venous plexus. The negative pressure on the lumbar anterior spinal venous plexus will draw cerebral spinal fluid (CSF) from the sub-arachnoid space. This increased egress of CSF from the sub-arachnoid space lowers the lumbar intrathecal pressure and by extension the ICP. To further direct the vector of the negative pressure toward the lumbar anterior spinal venous plexus, when the negative pressure is applied to the abdomen, one or more occlusive cuffs 70 may be applied to surround the upper portion of the patient's legs to decrease venous return from the legs as shown in FIG. 6.

Figure 6:
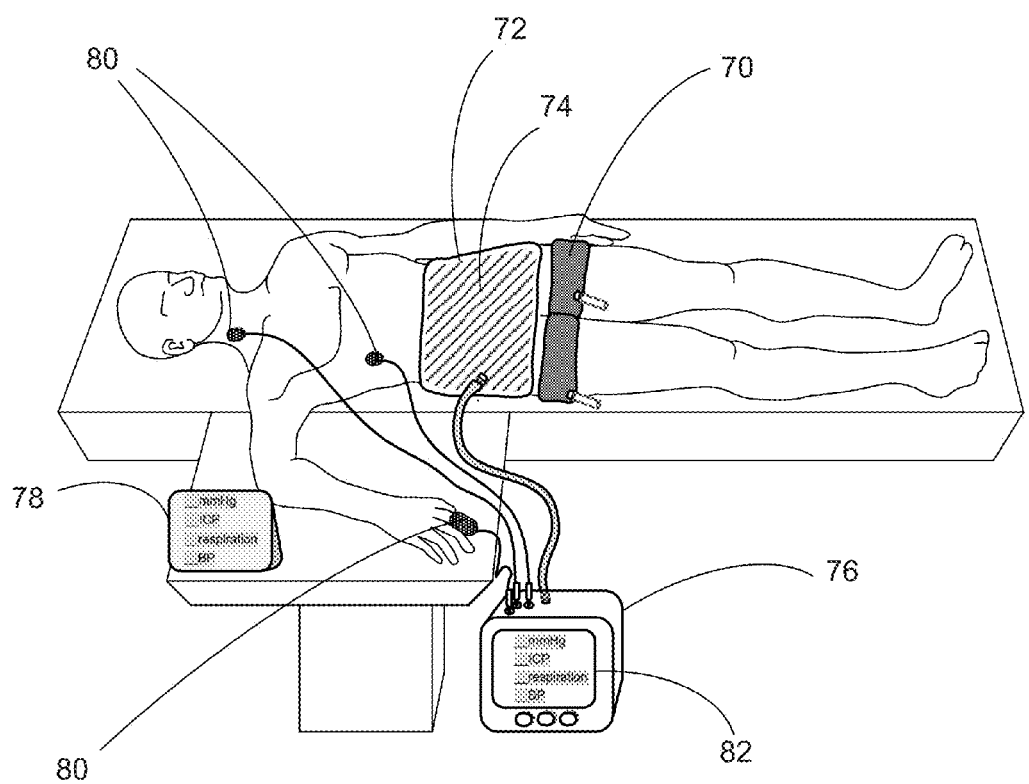
FIG. 6 depicts one embodiment of negative pressure system for application to a truck or abdominal region of a patient.

The cuffs may be pulled together to tighten or may be inflated through ports 71 as further depicted FIG. 6. Negative pressure is applied to the lower abdomen by evacuating a space within a pad or shell 72 placed around or across the abdomen. The pad or shell may be dimensioned to extend across a ventral aspect of the patient's abdomen or may encircle the patient as in a cuff or ring. A raised perimeter or gasket attached to the pad or shell fits against the patient's skin and forms a chamber that can be evacuate to apply negative pressure to a majority of the region of the lower abdomen of the patient. The negative pressure chamber 74 may be evacuated by a manual pump, particularly in emergency settings, or by using an electronically controlled programmable pump 76 that is set to apply negative pressure constantly, cycled based on the patient's inspiration, set to cycle at a preset rate, and/or synced with ICP monitoring. The pump housing may include a programmable controller or be controlled by a separate programmable computing device 78 that may be directly or wirelessly connected to the pump. Input from other parameters such as inspiration rate, blood pressure, cardiac output, pulmonary wedge pressure, jugular venous flow, etc. collected by one or more detection devices 80, the outputs of which are visible on display 82, may also be inputted to regulate application of negative pressure.

In another embodiment, a regional pressure chamber such as an iron lung is utilized to establish negative pressure around the chest and in doing so augment inspiration by increasing more negative inspiratory pressure. The negative inspiratory pressure reduces ICP and the patient is treated in the regional pressure chamber until ICP is stabilized.

Example 4: Negative Pressure System in Patients Using Breathing Assistance

One potential problem with application of negative pressure is that if the pressure in the cervical venous system is less than the pressure in the intrathoracic veins (innominate system) during inspiration, the venous blood could flow away from rather than towards the heart. Centrifugal cervical blood flow would quickly negate any potential ICP lowering effect. In most cases, particularly when the patient is breathing spontaneously, this pressure gradient reversal would not exist. However in patients on continuous positive airway pressure (CPAP) or positive end-expiratory pressure (PEEP), these gradients could exist and cause problems.

Flow devices, such as, for example, Doppler flow devices, may be employed to determine jugular venous flow. Placing such a device on the top of negative cervical collar over the jugular veins would provide real time data on jugular venous flow. In certain embodiments, this information is inputted into a computer device that adjusts the negative cervical pressure parameters if centrifugal jugular venous flow occurs. Parameters of the negative pressure application include the amount of negative pressure applied, the application rate, the pressure release rate, and the relationship to the patient's respiratory cycle. Input from other parameters such as cardiac output, pulmonary wedge pressure, etc. may also be inputted to regulate application of negative pressure.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. An intracranial pressure modulation apparatus comprising:
   a shell shaped and dimensioned to fit a ventral aspect of a neck of a patient;
   a negative pressure chamber positioned on an inner aspect of the shell, the negative pressure chamber comprising a peripheral gasket attached to an inner surface of the shell and adapted and dimensioned to form an outer perimeter of the negative pressure chamber between the shell and the ventral aspect of the neck of the patient, wherein the shell and gasket include a tracheotomy access opening and wherein the negative pressure chamber covers a sufficient portion of the ventral aspect of the patient's neck to effect a lowering of intracranial pressure through negative pressure transmitted to a vertebral venous system of the patient when negative pressure is applied but without extending to place positive or negative pressure on a carotid sinus of the patient;
   a suction port in communication with the negative pressure chamber to evacuate the negative pressure chamber; and
   at least one strap adapted and dimensioned to secure the shell to the patient's neck.

2. The apparatus of claim 1, further comprising a pump attached to the suction port via tubing.

3. The apparatus of claim 2, wherein the pump is controllable to cycle between negative pressure and zero pressure in synchrony with a respiration cycle of the patient.

4. The apparatus of claim 2, wherein the pump is controllable to cycle between negative pressure and zero pressure according to an inputted program.

5. The apparatus of claim 1, wherein the shell is one piece.

6. The apparatus of claim 1, wherein the shell is in more than one piece.

7. The apparatus of claim 1, wherein at least one negative pressure chamber is adapted to apply between 5 and 60 mmhg negative pressure to the ventral aspect region of the patient's neck.

8. The apparatus of claim 1, comprising at least two individual negative pressure chambers wherein at least one negative pressure chamber is positioned on each side of the tracheotomy access opening and wherein each individual negative pressure chamber comprises an individual suction port.

9. The apparatus of claim 8, wherein the individual suction ports are connected via suction hose to a single pump.

10. The apparatus of claim 1, wherein the negative pressure chamber comprises a single chamber with a central tracheotomy access opening sealed against the neck of the patient.

11. A system for decreasing intracranial pressure in a patient in need thereof comprising:
- a negative pressure chamber that is dimensional and adapted to fit against and cover a sufficient portion of a ventral aspect of a neck tissue of the patient to transmit negative cervical pressure to a vertebral venous system of the patient and effect a lowering of intracranial pressure when negative pressure is applied but without extending to place positive or negative pressure on a carotid sinus of the patient;
- a tracheotomy access opening;
- a programmable pump attached to the negative pressure chamber and dimensioned to apply between 5 and 60 mmhg negative pressure to the tissue; and
- an inspiration detector attached to the pump, wherein the pump pulls negative pressure on the tissue that is coincident with detected inspiration.

12. The system of claim 11, further comprising at least one occlusive band adapted and dimensioned to fit around a leg of the patient and retard venous return as desired.

13. The system of claim 11, comprising at least two individual negative pressure chambers wherein at least one individual negative pressure chamber is positioned on each side of the tracheotomy access opening and wherein each negative pressure chamber comprises an individual suction port.

14. The system of claim 11, wherein the negative pressure chamber comprises a single chamber with a central tracheotomy access opening sealed against the neck tissue of the patient.

\* \* \* \* \*